(12) United States Patent
Mahaffey et al.

(10) Patent No.: US 8,512,354 B2
(45) Date of Patent: Aug. 20, 2013

(54) DERMATOME BLADE ASSEMBLY

(75) Inventors: Mark Mahaffey, New Philadelphia, OH (US); Bruce Straslicka, Medina, OH (US)

(73) Assignee: Zimmer Surgical, Inc., Dover, OH (US)

( * ) Notice: Subject to any disclaimer, the term of this patent is extended or adjusted under 35 U.S.C. 154(b) by 61 days.

(21) Appl. No.: 13/180,831

(22) Filed: Jul. 12, 2011

(65) Prior Publication Data
US 2013/0018389 A1    Jan. 17, 2013

(51) Int. Cl.
*A61B 17/50* (2006.01)

(52) U.S. Cl.
USPC .......................................... 606/132

(58) Field of Classification Search
USPC .................... 16/2.1–2.5, 108, 109; 24/713.6, 24/713.7, 713.8; 30/32, 50, 329, 337, 339, 30/340, 342; 606/131, 132, 133
See application file for complete search history.

(56) References Cited

U.S. PATENT DOCUMENTS

| | | | |
|---|---|---|---|
| 2,457,772 A | 12/1948 | Barron et al. | |
| 3,428,045 A | 2/1969 | Kratzsch | |
| 3,583,403 A | 6/1971 | Keller | |
| 3,670,734 A | 6/1972 | Hardy | |
| 3,724,070 A * | 4/1973 | Dorion, Jr. | 30/47 |
| 3,820,543 A | 6/1974 | Vanjushin | |
| 3,857,178 A | 12/1974 | Stevens | |
| 4,038,986 A | 8/1977 | Mahler | |
| 4,098,278 A | 7/1978 | Schwartz | |
| 4,257,160 A | 3/1981 | Murai | |
| 4,754,756 A | 7/1988 | Shelanski | |
| 4,917,086 A | 4/1990 | Feltovich et al. | |
| 5,070,612 A * | 12/1991 | Abatemarco | 30/50 |
| 5,377,409 A * | 1/1995 | Chen | 30/41 |
| 5,588,191 A * | 12/1996 | Sølbeck | 24/713.6 |
| 5,873,881 A | 2/1999 | McEwen et al. | |
| 7,882,610 B2 * | 2/2011 | Gratsias et al. | 29/524.1 |
| 2009/0157095 A1 | 6/2009 | Barker et al. | |
| 2009/0157096 A1 | 6/2009 | Boles | |

* cited by examiner

*Primary Examiner* — Ryan Severson
*Assistant Examiner* — Jonathan W Miles
(74) *Attorney, Agent, or Firm* — Seager, Tufte & Wickhem, LLC

(57) ABSTRACT

A dermatome having a blade assembly, where the blade assembly includes a blade and a blade mount. The blade may include a blade edge, a reference edge and at least one hole or receiver positioned between the blade edge and the reference edge. The blade mount may include a base, a blade locator extending from the base and at least one reference fence abutting the reference edge of the blade. The blade locator may include a protrusion for inserting into the hole or receiver of the blade. The blade and blade mount of the blade assembly may self align and provide for a simple and permanent connection.

12 Claims, 12 Drawing Sheets

DERMATOME BLADE ASSEMBLY

TECHNICAL FIELD

The disclosure is directed to dermatomes for surgically harvesting grafts of skin. More particularly, the disclosure is directed to dermatome blade assemblies.

BACKGROUND

Conventional dermatomes are used for cutting skin tissue to obtain transplantable skin grafts. A skin graft is a patch of healthy skin that is harvested from one area of the body or donor site to cover a damaged or skinless area of the body. Typically, a dermatome has a front end holding a flat blade to be placed in contact with a tissue surface and a motor to oscillate the blade from side to side to create a slicing action which cuts the tissue as the dermatome is moved along the tissue surface.

SUMMARY

The disclosure is directed to several alternative designs, materials and methods of manufacturing medical device structures and assemblies. Although it is noted that conventional dermatomes exist, there exists a need for improvement of those devices.

Accordingly, one illustrative embodiment of the disclosure may include a dermatome blade assembly having a blade and a blade mount, where the blade and the blade mount are connected to one another. The blade may include a blade edge, a reference edge spaced from the blade edge and at least one receiver positioned between the blade edge and the reference edge. The blade mount may include a base, at least one blade locator and at least one reference fence. In alignment, the at least one reference fence may contact the reference edge and the at least one blade locator may communicate with the at least one receiver. The alignment and connection of the blade with the blade mount may allow for an aligned and simply assembled blade assembly without the use of complicated or time consuming manufacturing techniques.

The above summary of some example embodiments is not intended to describe each disclosed embodiment or every implementation of the disclosure.

BRIEF DESCRIPTION OF THE DRAWINGS

The disclosure may be more completely understood in consideration of the following detailed description of various embodiments in connection with the accompanying drawings, in which.

Figure 1:
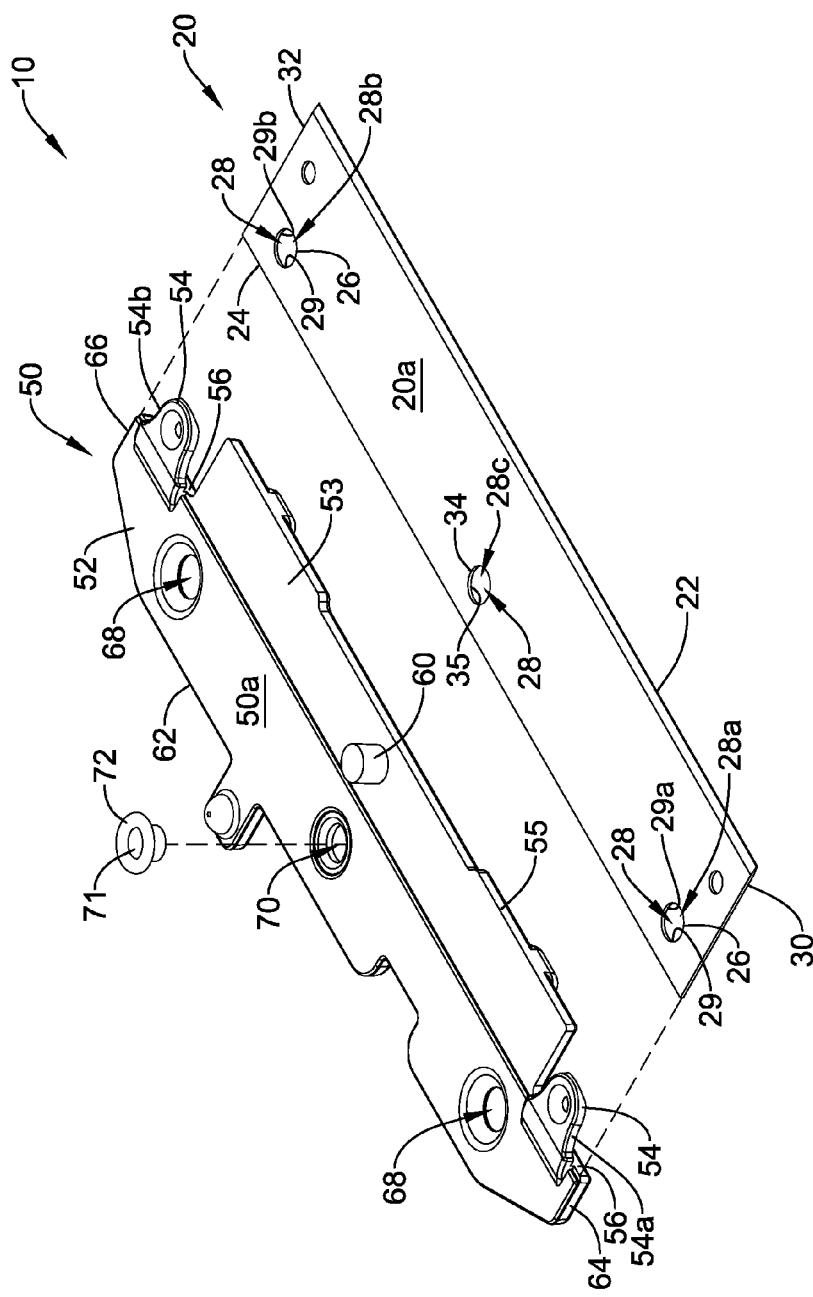
FIG. 1 is an exploded perspective view of a dermatome blade assembly according to an aspect of the disclosure.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the claimed disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the claimed disclosure. The illustrative embodiments depicted are intended only as exemplary. Selected features of any illustrative embodiment may be incorporated into an additional embodiment unless clearly stated to the contrary.

The present disclosure relates to the subject matter filed by inventors Mark Mahaffey and Bruce Straslicka and contained in the U.S. patent application titled DERMATOME BLADE ASSEMBLY GUARD having attorney docket no. 1001.1007101 and the U.S. patent application titled DERMATOME WITH WIDTH PLATE CAPTURES having attorney docket no. 1001.1006101, both filed on Jul. 12, 2011, and which are both expressly incorporated herein by reference in their entirety.

Referring to FIGS. 1-10, a dermatome 110 for harvesting skin grafts of tissue may include a blade assembly 10 having a blade 20 and a blade mount 50. Blade 20 may include a blade edge 22, a reference edge 24 opposite blade edge 22, and at least one receiver 26 that may be positioned at least partially between blade edge 22 and reference edge 24. Receiver(s) 26 may include a first hole or opening 28a and a second hole or opening 28b, where holes 28a, 28b may be transversely spaced along blade 20 and may be positioned between blade edge 22 and reference edge 24. Blade mount 50 may include a base 52, an overlap portion 53, at least one blade locator 54 and at least one reference fence 56, where blade locator 54 may extend from base 52 and be offset from overlap portion 53 to receive blade 20 therebetween. Blade locator(s) 54 may include a first detent 58a (e.g., knob, extension, lip, protrusion, bump, etc.) and a second detent 58b (e.g., knob, extension, lip, protrusion, bump, etc.) protruding therefrom, where detents 58a, 58b may extend within holes 28a, 28b of receiver(s) 26 when assembled. When receiver(s) 26 align with blade locator(s) 54 and reference edge 24 contacts reference fence(s) 56, blade assembly 10 may be properly aligned for permanent assembly and use.

The Blade

Figure 2:
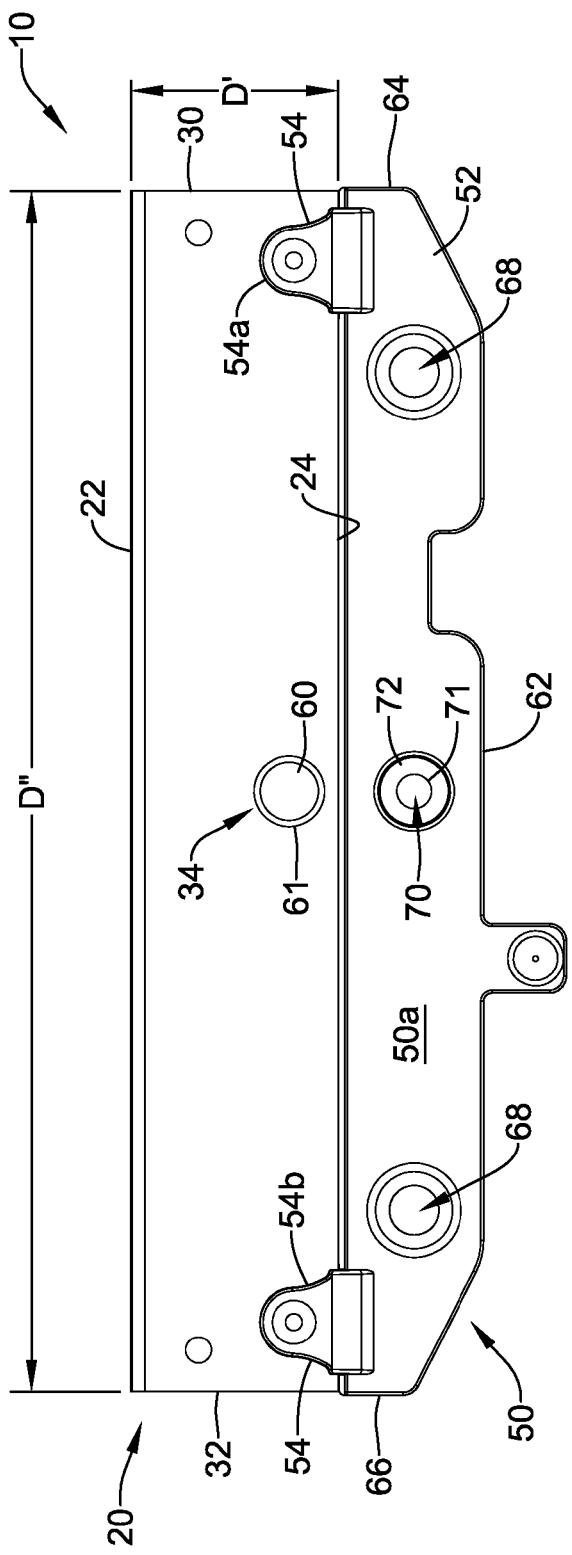
FIG. 2 is a top view of the dermatome blade assembly depicted in FIG. 1.

As seen in FIGS. 1-4 and 8, blade 20 may include a first end edge 30 and a second end edge 32 opposite first end edge 30, where edges 30, 32 may extend between blade edge 22 and reference edge 24 at opposite ends of blade 20. End edges 30, 32 may have any desirable dimensions. For example, as seen in FIG. 2, end edges 30, 32 may have similar dimensions and may extend a first distance D', which may be less than (as shown) or greater than a second distance D" that blade edge 22 spans between end edges 30, 32. Receiver(s) 26 of blade edge 22 may be a hole or opening 28 in, on, or through blade 20, where opening(s) 28 may have a perimeter 29 defining openings 28 therein.

Figure 4:
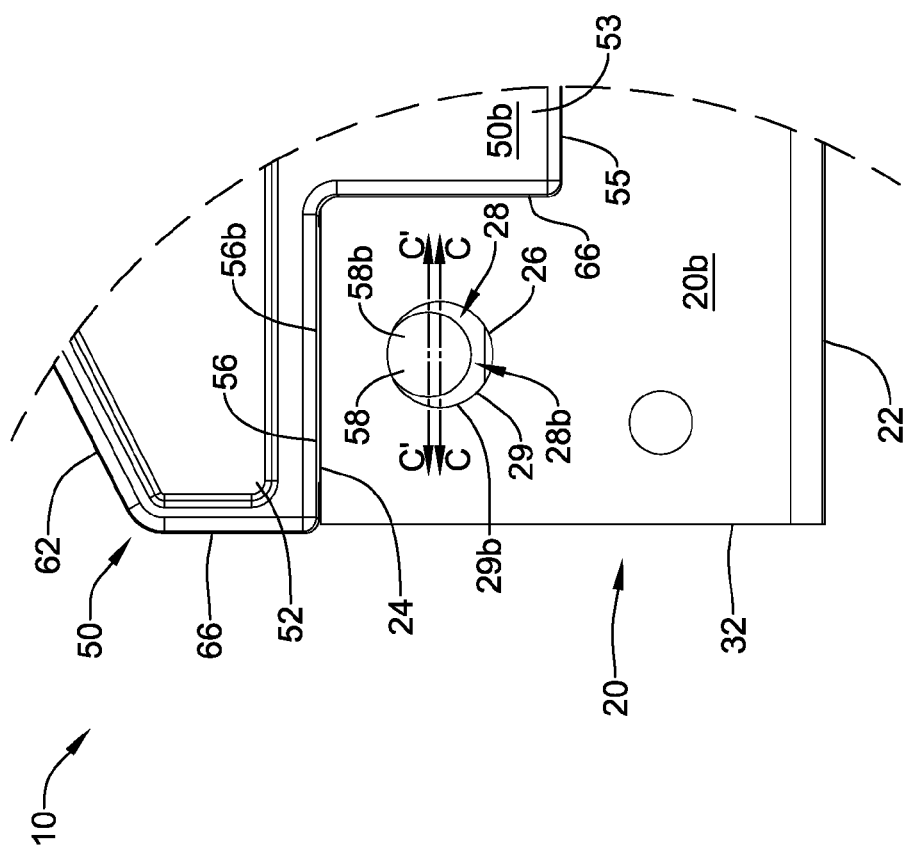
FIG. 4 is an enlarged bottom view of a portion of the dermatome blade assembly depicted in FIG. 3.
Figure 8:
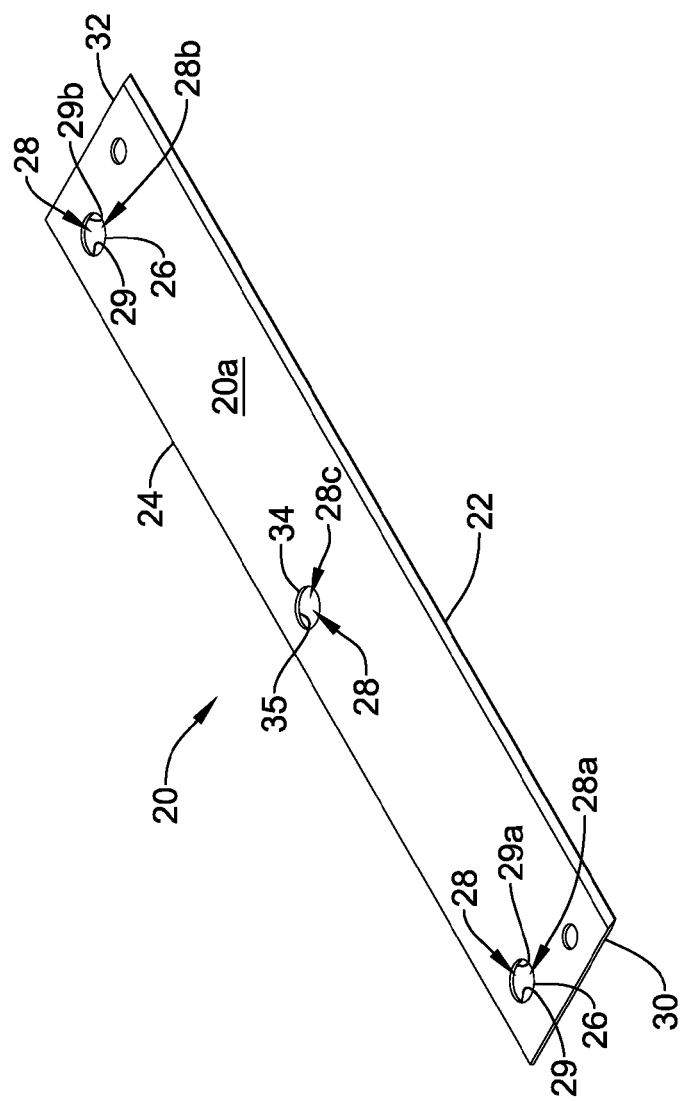
FIG. 8 is a back perspective view of blade features of a dermatome blade assembly according to an aspect of the disclosure.

Receiver 26 may include a first receiver 26a having first opening 28a and a second receiver 26b having second opening 28b, where holes or openings 28a, 28b may be at least partially defined by a first perimeter 29a and a second perimeter 29b, respectively, and each opening 28a, 28b may have a central line or axis C-C extending there through, as seen in FIGS. 4 and 8, which may be parallel to blade edge 22 and/or reference edge 24. Receiver(s) 26 may be located at any position on or in blade 20. For example, receiver(s) 26 may be at least partially defined by blade 20 and may extend from a first side 20a to a second side 20b of blade 20. Receivers 26 may be capable of receiving at least a portion of detent 58 extending from blade locator 54, where detent 58 extends from blade locator 54 in a direction of receiver 26.

Blade 20 may include a stake receiver 34, as seen in FIGS. 1, 2 and 8-9C. Stake receiver 34 may have a perimeter 35 defining boundaries of receiver 34, where perimeter 35 is at least partially defined by blade 20. Stake receiver 34 may have any shape or size having boundaries set by perimeter 35. For example, as seen in FIGS. 8 and 9A-9C, stake receiver 34 may be a hole or opening 28 (e.g., a third hole 28c) extending from first side 20a to second side 20b of blade 20. Opening 28c of receiver 34 may have a cross-section slightly larger than a cross-section of a mount stake 60 extending from blade mount 50 so as to be capable of receiving mount stake 60 there through, where the cross-sections of stake receiver 34 and stake 60 may be similarly shaped and may both have substantially circular cross-sections or cross-sections of other shapes, similar or not. Hole 28c of receiver 34 may be positioned at any location at least partially within end edges 30, 32, blade edge 22 and reference edge 24. For example, hole 28c may be positioned entirely within edges 22, 24, 30, 32 and may be spaced equidistant from first hole 28a and second hole 28b, in some instances.

Blade 20 may be made of any material capable of providing the described blade 20. For example, blade 20 may be made of a metal material such as a steel or any other suitable material.

The Blade Mount

As seen in FIGS. 1-7 and 9A-9C, blade mount 50 may include base 52 at least partially defined by a front edge 55, reference fence 56, a profile edge 62, a first mount end 64 and a second mount end 66. Ends 64, 66, fence 56 and edges 55, 62 may form a perimeter defining base 52. Base 52 may further include at least one fastening hole 68 at least partially defined therein, as shown in FIGS. 1-3, 5, 7 and 9A-9C. Fastening hole(s) 68 may be used for any purpose; for example, fastening hole(s) 68 may be capable of receiving a fastener for attachment to a main body 100 or other object. For instance, fastening hole(s) 68 may be configured to receive alignment posts or protuberances of a blade guard or other detachable component.

Blade mount 50 may be made from a unitarily formed piece of material or multiple pieces connected to form blade mount 50, where each piece is made of the same or a different material. Blade mount 50 may be made of any material known in the art capable of being formed or manufactured as described herein. For example, base 52 may be made of a plastic material.

Figure 3:
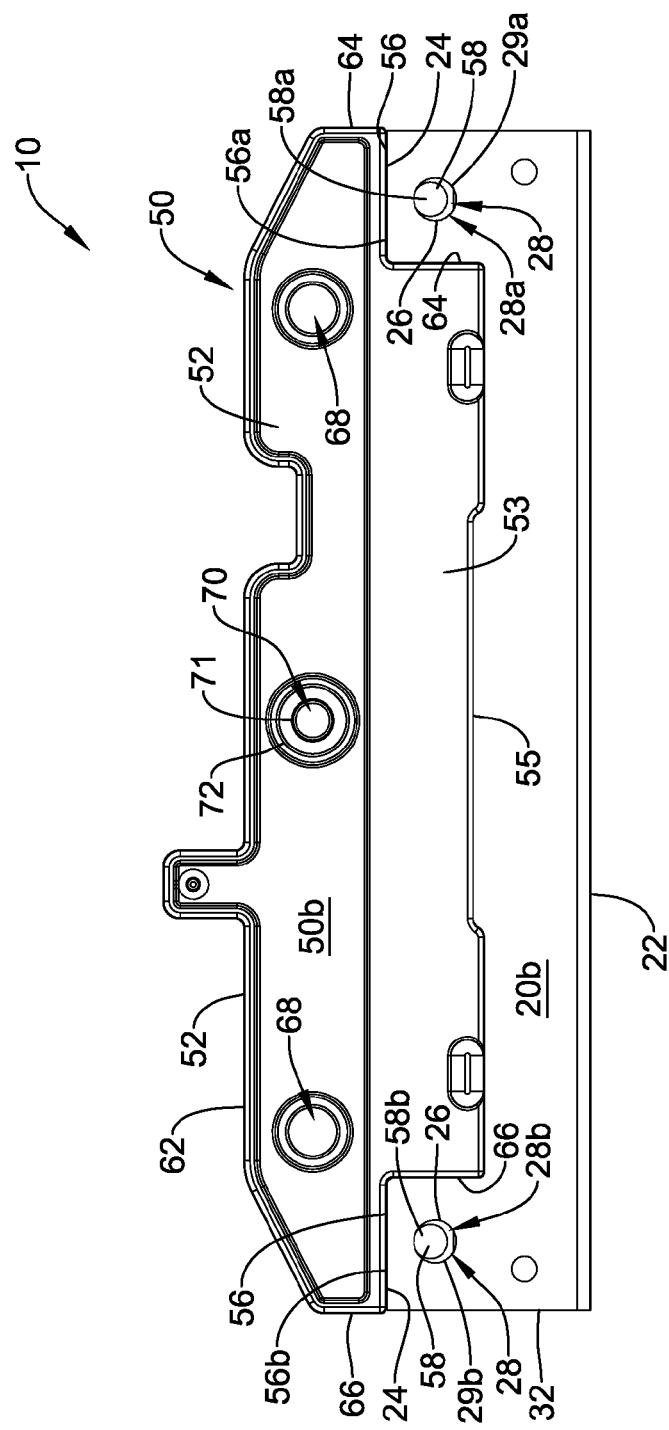
FIG. 3 is a bottom view of the dermatome blade assembly depicted in FIG. 1.
Figure 6:
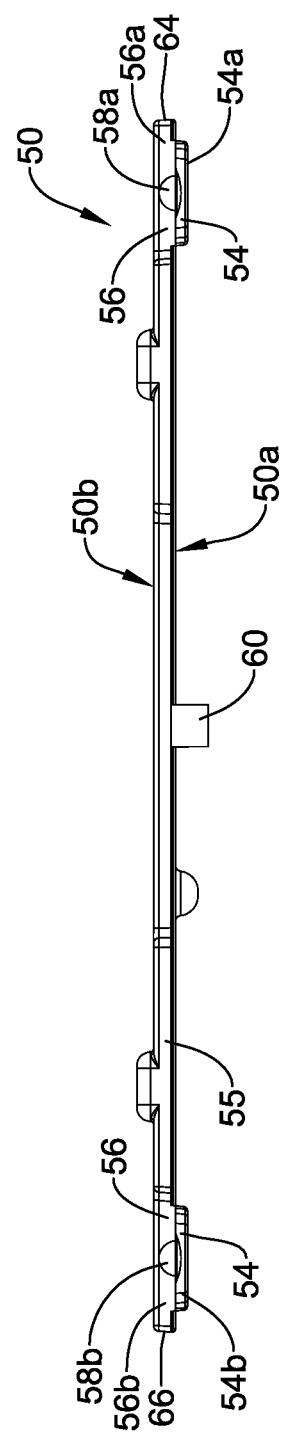
FIG. 6 is a front view of the blade mount features depicted in FIG. 5.

Blade mount 50 may include at least one reference fence 56. For example, blade mount 50 may include a first reference fence 56a and a second reference fence 56b, where reference fences 56a, 56b may be spaced apart, as depicted in FIGS. 3 and 6. In the example, reference fences 56a, 56b may be proximate mount ends 64, 66 and extend inward from ends 64, 66. Reference fence 56, in operation, may abut or contact reference edge 24 of blade 20 when blade assembly 10 is assembled or at other times.

Base 52, as depicted in FIGS. 1-3, 5 and 9A-9C, may have a drive eyelet 70. Drive eyelet 70 may be at least partially defined by base 52 and may have a perimeter 71 having a substantially circular cross-section. Drive eyelet 70 may be used for any purpose. For example, as seen in FIG. 10, drive eyelet 70 may be configured to receive an oscillating pin 102 extending from main body 100 when blade assembly 10 is mounted on a main body 100 of a dermatome 110. In the example, pin 102 may oscillate within eyelet 70 to provide reciprocating motion to blade assembly 10.

Drive eyelet 70 may be made out of any material. For example, a hole forming drive eyelet 70 may be formed within a plastic or other material of base 52 and the hole forming drive eyelet 70 may be reinforced with a drive eyelet cap 72 made of a metal or another suitable material. In the example, an illustrative metal material may be a brass material, a stainless steel material, or any other metal. The metal may reinforce drive eyelet 70 to limit or prevent damage caused by oscillating pin 102 coming into contact with perimeter 71 of drive eyelet 70.

As seen in FIGS. 1, 2, 5-7 and 9A-9C, blade mount 50 may include blade locators 54 extending from base 52. Blade locators 54 may extend from any portion of base 52. For example, blade locators 54 may extend from first side 50a of base 52, second side 50b of base 52 or reference fence 56 or a combination thereof or any other location on base 52 that allows reference edge 24 of blade 20 to contact reference fence 56. Blade locators 54 may extend from base 52 toward blade 20 and may contact an engaged blade 20 on at least first side 20a or at another location on blade 20. Locators 54 may have detent 58 or other protrusion extending from a surface of locator 54 toward and/or into engagement with receiver 26. Detents 58 may extend from locator 54 in any direction capable of engaging receiver 26. For example, detents 58 may extend in a direction generally transverse to a plane of first side 50a. Detents 58 may be used for any purpose and in an example, detents 58 may be utilized for locating and engaging blade 20 and aligning blade mount 50 with blade 20 for final connection.

Figure 5:
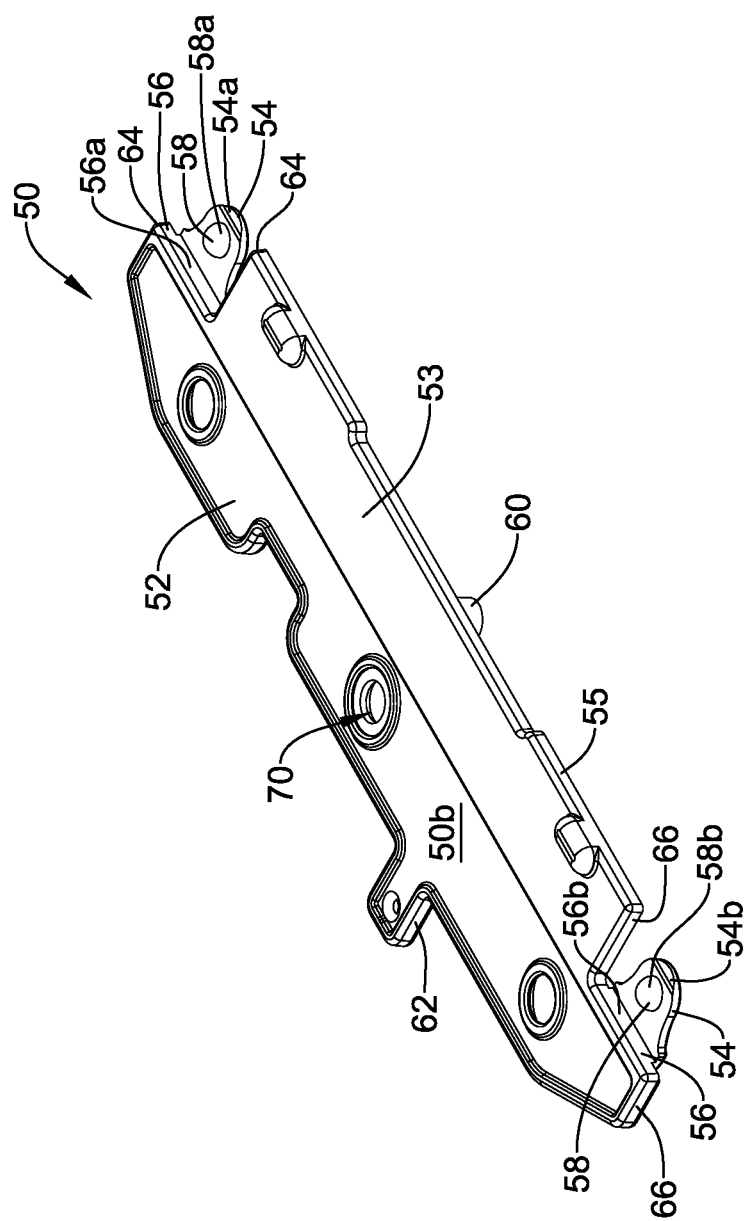
FIG. 5 is a front perspective view of blade mount features of a dermatome blade assembly according to an aspect of the disclosure.
Figure 7:
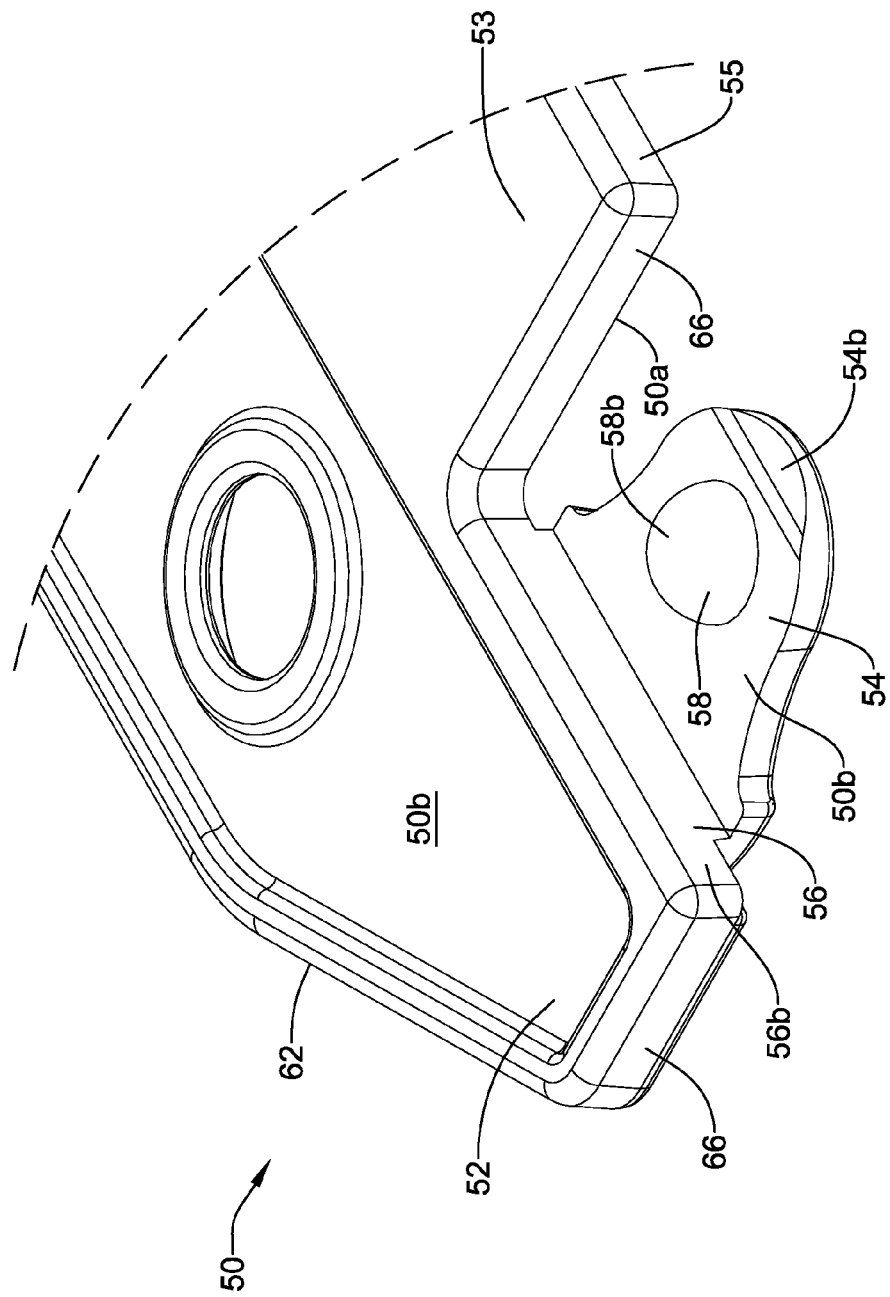
FIG. 7 is an enlarged perspective view of a portion of the blade mount features depicted in FIG. 5.

Locator(s) 54 may be offset from base 52, as seen in FIGS. 5, 6 and 7 to allow blade 20 to be positioned between overlap portion 53 and locator(s) 54. The off-set may allow blade mount 50 to receive blade 20 between first side 50a of base and second side 50b of locator 54 with reference fence 56 extending between first side 50a of overlap portion 53 of base 52 and second side 52b of locator 54 to contact reference edge 24 of blade 20. Blade 20 may be received within blade mount 50 such that first side 20a of blade 20 may contact second side 50b of locator 54 and second side 20b of blade 20 may contact first side 50a of overlap portion 53 of base 52, as seen in FIGS. 1-3.

Once locator 54 (e.g., detent 58 of locator 54) locates blade 20 and receiver 26, detents 58a, 58b may engage holes or openings 28a, 28b. Detents 58a, 58b may abut or contact portions of perimeters 29 nearest reference edge 24 so as to be off-centered within perimeter 29 of receivers 26. Off-centered may mean positioning detents 58a, 58b in respective openings 28a, 28b such that a central line or axis C'-C' across detents 58a, 58b (parallel to central line or axis C-C, and thus parallel to blade edge 22 and/or reference edge 24) is not in alignment with central line or axis C-C across openings 28a, 28b, as shown in FIG. 4. Blade 20 and blade mount 50 may communicate with one another such that when detents 58a, 58b are off-centered within openings 28a, 28b, detents 58a, 58b may press against perimeters 29 and reference edge 24 may press against reference fence 56. Thus, detent 58 may be positioned at any location on locator 54 allowing for detent 58 to be spaced a requisite distance from reference fence 56 such that when detent 58 contacts perimeter 29, reference edge 24 is pressed into contact with reference fence 56 to align blade 20 with blade mount 50. The contact between detents 58a, 58b and perimeters 29, along with the contact between reference edge 24 and reference fence 56, may limit movement of blade 20 with respect to blade mount 50 in at least first and second opposing directions lying in the plane of blade 20 and/or third and fourth opposing directions lying in the plane of blade 20 perpendicular to first and second directions. In some instances, engagement of detents 58a, 58b of locators 54 of blade mount 50 in openings 28a, 28b of blade 20, as well as aligning reference edge 24 against reference fence 56 while blade 20 is positioned between surfaces of locators 54 and a surface of overlap portion 53 of base 52 (with first side 20a of blade 20 facing locators 54 and second side 20b of blade 20 facing overlap portion 53 of base 52) prevents relative movement between blade 20 and blade mount 50 in all directions.

A stake 60 may extend from first side 50a or second side 50b of base 52 and may be positioned at any location on base 52, where stake 60 may be capable of extending through stake receiver 34 of blade 20. For example, stake 60 may extend from first side 50a of base 52 and may be located equidistant from a first blade locator 54a and a second blade locator 54b. Stake 60 may be integrally formed with base 52 or stake 60 (e.g., base 52 and stake 60 may be a unitary structure) may be connected with base 52 by any known connection technique. Further, stake 60 may be made of any material and may be made of the same or similar material with which base 52 is formed.

The Assembly

Figure 9A:
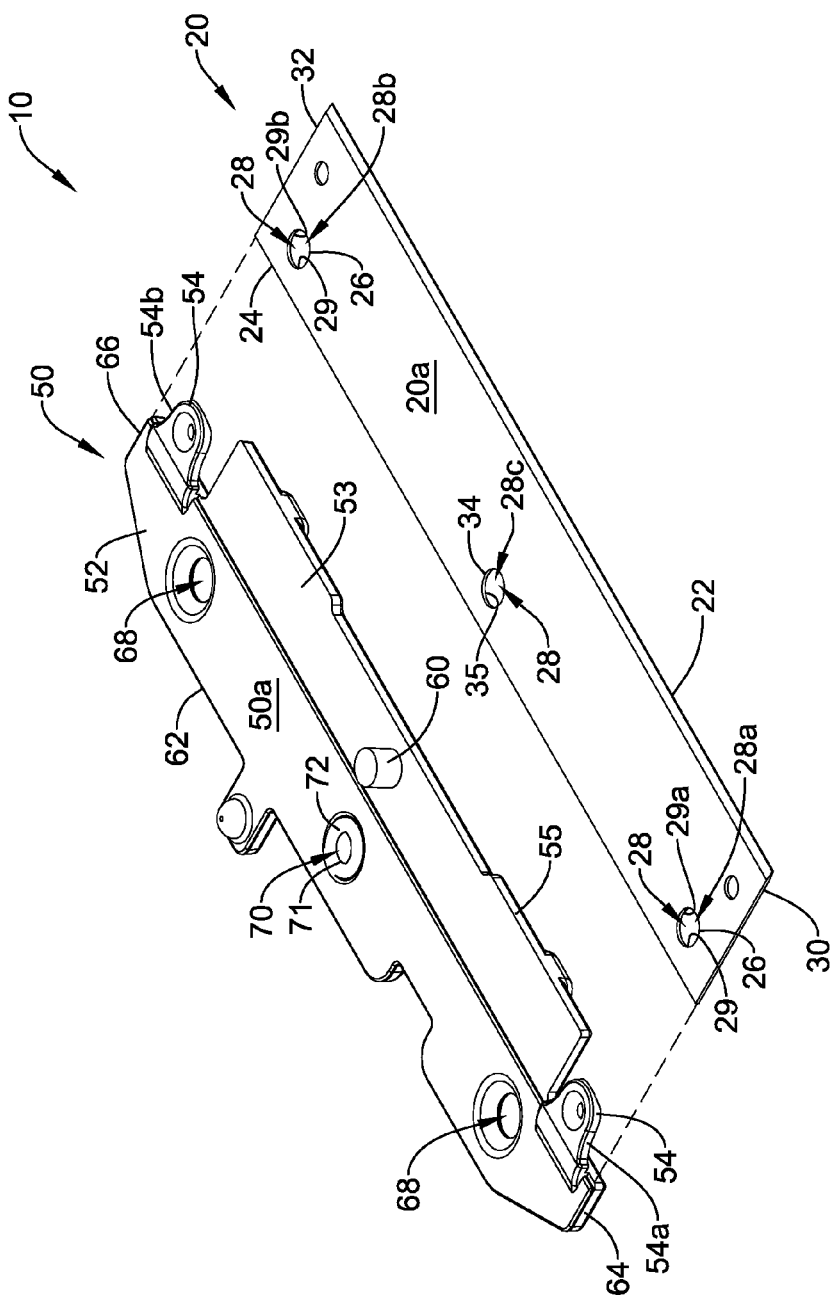
FIGS. 9A-9C depict a dermatome blade assembly in various stages of being assembled according to an aspect of the disclosure.
Figure 9B:
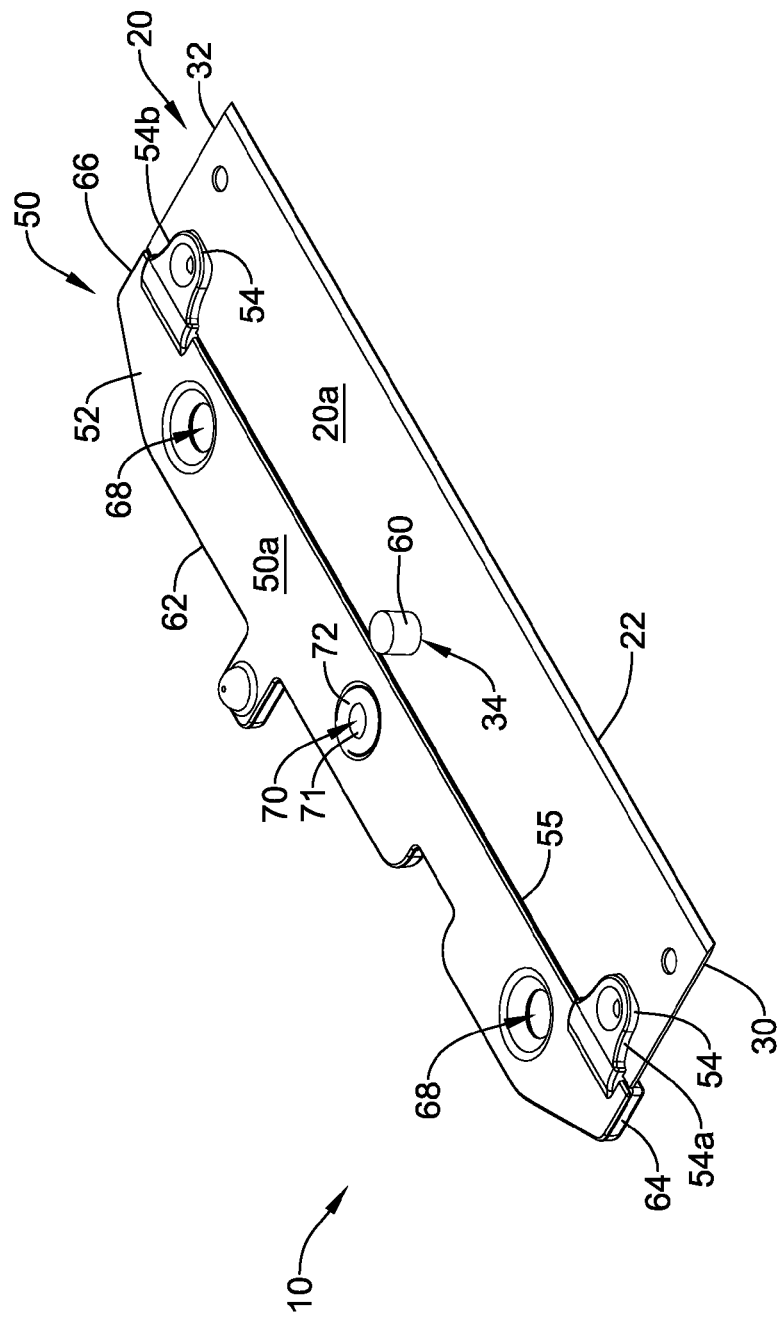
Figure 9C:
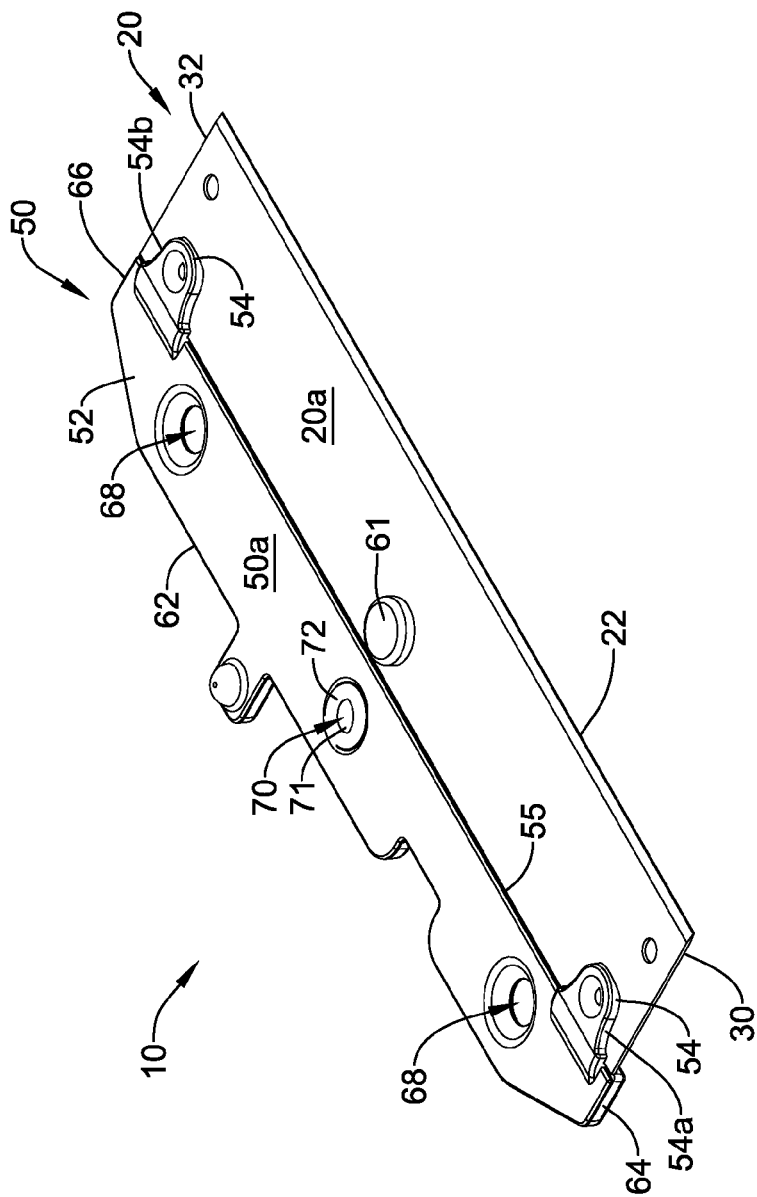
Figure 10:
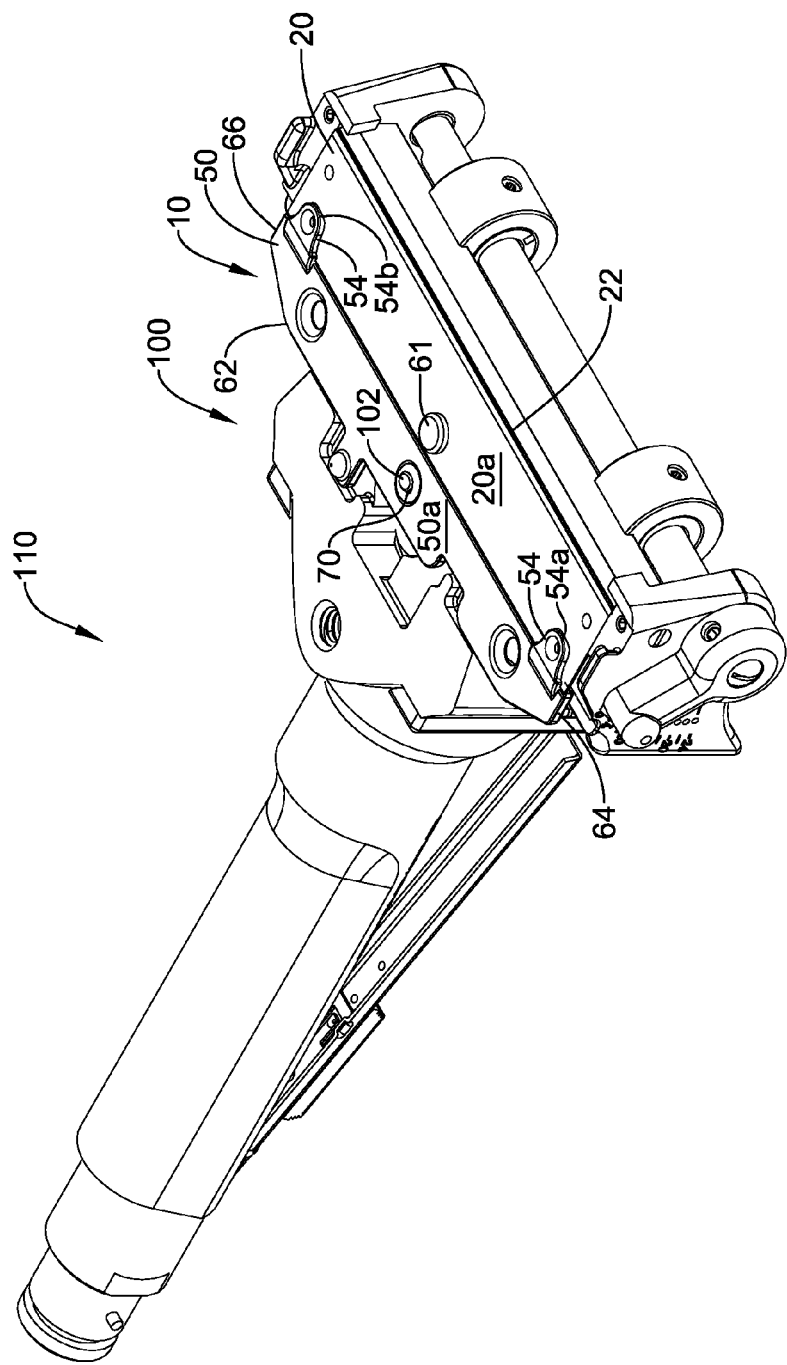
FIG. 10 is a bottom view of a dermatome according to an aspect of the disclosure.

Blade assembly 10 may allow for simple aligning and connecting of blade 20 with blade mount 50, as seen in FIGS. 9A-9C. In an illustrative assembly, blade 20 may be slid into contact with blade mount 50 (e.g., between locators 54 and overlap portion 53) and reference edge 24 of blade 20 may be abutted with reference fence 56 of blade mount 50 such that first side 20a of blade 20 may contact second side 50b of locator 54 and second side 20b of blade 20 may contact first side 50a of overlap portion 53 of base 52. At a same or similar time, detents 58a, 58b of blade locators 54 may be aligned with and inserted in openings 28a, 28b. Detents 58a, 58b may be partially or fully inserted into openings 28a, 28b. For example, detents 58a, 58b may be inserted into openings 28a, 28b such that first side 50a of blade locator 54 contacts second side 20b of blade 20 adjacent openings 28a, 28b. Detents 58a, 58b may be oriented in an off-centered manner with respect to a central line C-C of holes or openings 28a, 28b of receivers 26, as seen in FIGS. 3 and 4. That is, detents 58a, 58b may contact perimeters 29 of holes or openings 28a, 28b when in the off-centered orientation.

Once blade 20 and blade mount 50 have been aligned through inserting detents 58 into receivers 26 and/or abutting reference edge 24 with reference fence 56, or during alignment, blade mount 50 may be connected to blade 20 by engaging the two pieces 50, 20 or by another operation. The connection may be a permanent connection or a nonpermanent connection. A permanent connection may be an irreversible connection where two or more pieces that are connected cannot be unconnected without materially altering at least one of the pieces or deforming at least one piece. The engagement between blade mount 50 and blade 20 may be accomplished by inserting mount stake 60 of blade mount 50 into and through stake receiver 34 of blade 20. To finalize the engagement between the blade 20 and blade mount 50, inserted stake 60 may be heated and/or deformed to form a button 61. When hardened and/or deformed, button 61 may contact and overlap first side 20a of blade 20 such that blade 20 may not be separated from blade mount 40 without materially altering the formed button 61 or other portions of blade mount 50 or blade 20. Once blade assembly 10 is assembled, it may be mounted on a main body 100 of a dermatome 110 or blade assembly 10 may be used for any other purpose.

The disclosed blade assembly 10 may eliminate or mitigate the need to measure a location of blade 20 with respect to blade mount 50 because of the included receivers 26, blade locators 54, reference edge 24, reference fence 56 and other features that may work together to precisely align blade 20 and blade mount 50.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A dermatome blade assembly, comprising:
    a blade including:
        a blade edge;
        a reference edge spaced from the blade edge; and
        at least one receiver positioned between the blade edge and the reference edge;
    a blade mount including:
        a base;
        at least one blade locator extending from the base; and
        at least one reference fence, and
    wherein the at least one reference fence of the blade mount abuts the reference edge of the blade, and
    wherein the at least one receiver is aligned with the at least one blade locator and the aligned at least one blade locator urges the reference edge against the at least one reference fence; further comprising a detent protruding from the at least one blade locator and the detent extending into the at least one receiver, wherein the at least one receiver is an opening extending through the blade and the opening has a perimeter, and wherein the detent contacts the perimeter of the opening and the detent is off-centered within the opening.

2. The dermatome blade assembly of claim 1, further comprising:

a stake receiver at least partially defined by the blade; and a mount stake extending from the base through the stake receiver.

3. The dermatome blade assembly of claim 2, wherein the mount stake extending through the stake receiver is deformed to form a button and permanently connect the blade to the blade mount.

4. The dermatome blade assembly of claim 3, wherein the blade is formed of metal and the blade mount is formed of plastic.

5. The dermatome blade assembly of claim 1, further comprising:

a blade drive eyelet positioned in the blade mount, the blade drive eyelet configured to receive an oscillating pin to provide reciprocating motion to the blade assembly, and wherein the blade mount is made of a plastic material and the blade drive eyelet is reinforced with a metal material.

6. A blade assembly for a dermatome, the blade assembly comprising:

a blade having a first side and a second side, the blade including:

a blade edge;

a reference edge spaced from the blade edge;

a first hole extending through the blade; and a second hole extending through the blade, and wherein the first and second holes are spaced apart transversely along the blade and are positioned between the blade edge and the reference edge, and a blade mount coupled to the blade, the blade mount including:

a first detent extending within the first hole of the blade;

a second detent extending within the second hole of the blade; and a reference fence;

wherein the first detent extending within the first hole of the blade and the second detent extending within the second hole of the blade urge the reference edge of the blade against the reference fence of the blade mount, wherein the first detent is off-centered within the first hole and the second detent is off-centered within the second hole.

7. The blade assembly of claim 6, wherein the reference fence abuts substantially an entirety of the reference edge.

8. The blade assembly of claim 7, wherein the blade includes a third hole, and wherein the blade mount includes a mount stake inserted through the third hole.

9. The blade assembly of claim 8, wherein the third hole is positioned equidistant from the first hole and the second hole.

10. The blade assembly of claim 6, wherein the first detent abuts an edge of the first hole and the second detent abuts an edge of the second hole, and wherein contact between the detents and a peripheral edge of the holes urges the reference edge of the blade against the reference fence of the blade mount.

11. The blade assembly of claim 6, wherein the blade mount includes first and second blade locators positionable on the first side of the blade, and the blade mount including an overlap portion positionable on the second side of the blade;

wherein the first detent extends from the first blade locator and the second detent extends from the second blade locator.

12. The blade assembly of claim 11, wherein the first and second blade locators are offset from the overlap portion, and the reference fence is configured to abut the reference edge when the blade is positioned between the first and second blade locators and the overlap portion.

* * * * *